United States Patent [19]
Urbahns et al.

[11] Patent Number: 6,159,215
[45] Date of Patent: Dec. 12, 2000

[54] INSERTION INSTRUMENTS AND METHOD FOR DELIVERING A VERTEBRAL BODY SPACER

[75] Inventors: David J. Urbahns, Beachwood; Dale G. Davison, Westlake, both of Ohio; Kenneth Danylchuk; James C. Luczak, both of Pueblo, Colo.; Ronald Moskovich, Mamaronek, N.Y.; Thomas Camino, Warsaw; Joel C. Rhoades, Pierceton, both of Id.

[73] Assignee: Depuy Acromed, Inc., Raynam, Mass.

[21] Appl. No.: 09/216,440

[22] Filed: Dec. 18, 1998

Related U.S. Application Data

[60] Provisional application No. 60/071,527, Jan. 15, 1998, and provisional application No. 60/068,205, Dec. 19, 1997.

[51] Int. Cl.$^7$ ................................................ A61F 5/00
[52] U.S. Cl. ............................................................... 606/86
[58] Field of Search ............................ 606/99, 86; 623/17, 623/17.11

[56] References Cited

U.S. PATENT DOCUMENTS

| 4,834,757 | 5/1989 | Brantigan . |
| 4,878,915 | 11/1989 | Brantigan . |
| 4,997,432 | 3/1991 | Keller . |
| 5,192,327 | 3/1993 | Brantigan . |
| 5,425,772 | 6/1995 | Brantigan . |
| 5,431,658 | 7/1995 | Moskovich . |
| 5,458,638 | 10/1995 | Kuslich et al. . |
| 5,522,899 | 6/1996 | Michelson . |
| 5,554,191 | 9/1996 | Lahille et al. . |
| 5,591,235 | 1/1997 | Kuslich . |
| 5,609,636 | 3/1997 | Kohrs et al. . |
| 5,609,637 | 3/1997 | Michelson . |
| 5,658,337 | 8/1997 | Kohrs et al. . |
| 5,669,909 | 9/1997 | Zdeblick et al. . |
| 5,702,449 | 12/1997 | McKay . |
| 5,716,415 | 2/1998 | Steffee . |

FOREIGN PATENT DOCUMENTS 0268156  5/1989  Germany .................................. 606/99

OTHER PUBLICATIONS

"The DePuy Motech Surgical Titanium Mesh, The Right Size, The Right Shape, Right Now," 10M595 0604–29–000 (Rev. 1), ©1994 DePuy Motech Inc. (1 page).

"Surgical Titanium Mesh Product Catalogue," #9067–14 DePuy Motech Inc. (10 pages). (No Date).

(List continued on next page.)

Primary Examiner—Jeffrey A. Smith
Attorney, Agent, or Firm—Barnes & Thornburg

[57] ABSTRACT

A spacer-insertion instrument for delivering a spacer to a spine is disclosed. The instrument includes a handle portion and a guide coupled to the handle portion. The instrument further includes a shaft coupled to the handle portion and extending along the guide. The instrument further includes a tip including an attachment end portion coupled to the shaft and opposing fingers movable relative to one another and adapted to grasp the spacer when the shaft is moved to actuate the fingers. The handle portion includes a grip and a trigger coupled to the grip and to the shaft and movement of the trigger toward the grip causes the fingers to move toward one another. A method for delivering a vertebral body spacer to a disc space formed in a spine between adjacent vertebral bodies is also disclosed.

19 Claims, 6 Drawing Sheets

OTHER PUBLICATIONS

"Moss® Modular Segemental Spinal Instrumentation Product Catalogue," #9067–15 DePuy Motech Inc. (6 pages). (No Date).

J. Harms, M.D., "Screw–Threaded Rod System in Spinal Fusion Surgery," SPINE: State of the Art Reviews—vol. 6, No. 3, Sep. 1992, pp. 541–575.

"Bench Test Report DM–003 Titanium Surgical Mesh, Evaluation of Titanium Surgical Mesh in Multiple Static Compressive Loading Scenarios," #5M496, 0604–50–000, ©1996 DePuy Motech, Inc. (3 pages).

Gary L. Lowery and Jürgen Harms, "Titanium Surgical Mesh for Vertebral Defect Replacement and Intervertebral Spacers," Manual of Internal Fixation of The Spine, edited by John S. Thalgott and Max Aebi, Lippincott–Raven Publishers, Philadelphia, ©1996, pp. 127–146.

"Bench Test Report DM–004 Titanium Surgical Mesh, Evaluation of Titanium Surgical Mesh in High Cycle Fatigue Loading Scenarios," #5M496, 0604–51–000, ©1996 DePuy Motech, Inc. (3 pages).

J. Harms and D. Stoltze, "The Indications and Principles of Correction of Post–Traumatic Deformities", Eur. Spine J. (1992) 1:142–151.

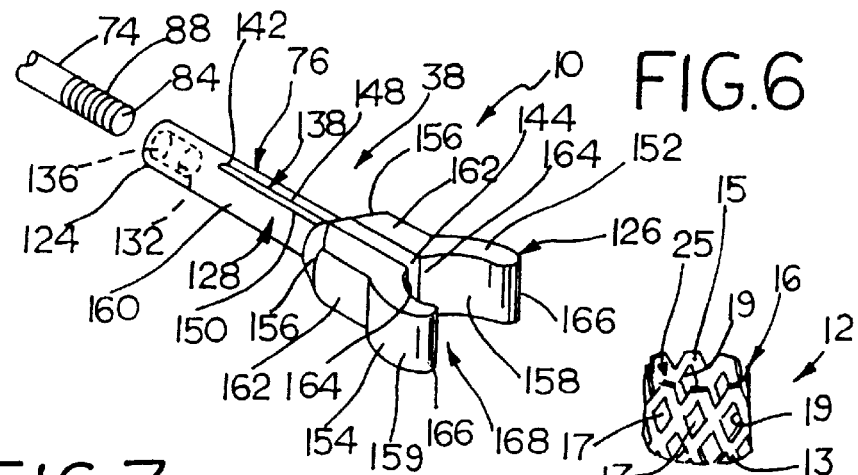
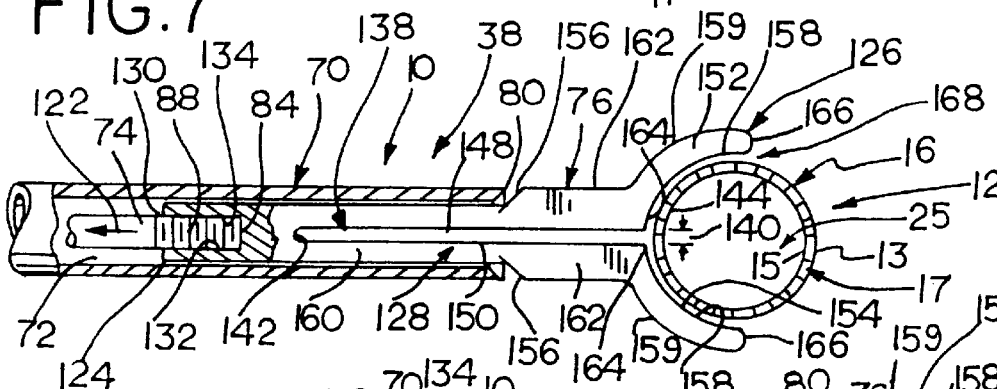
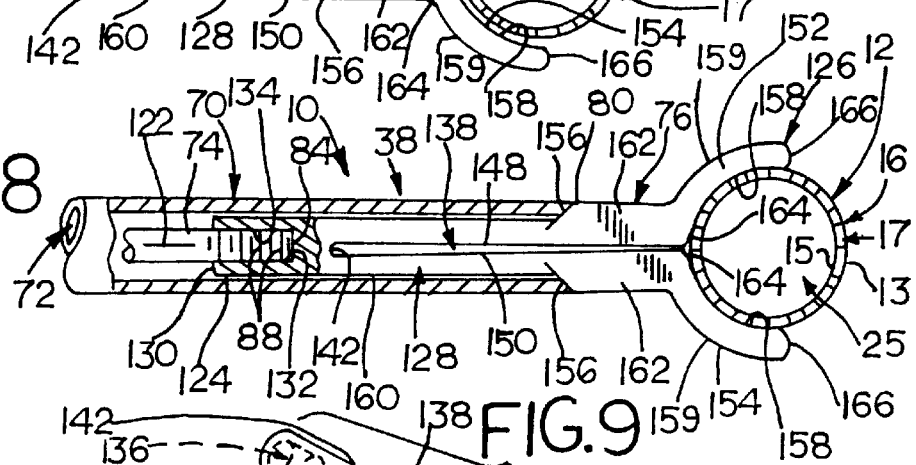
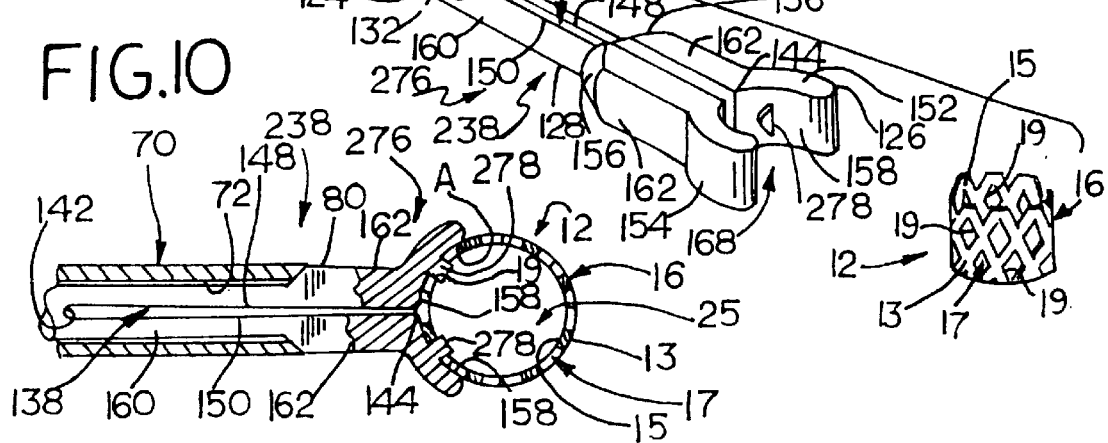

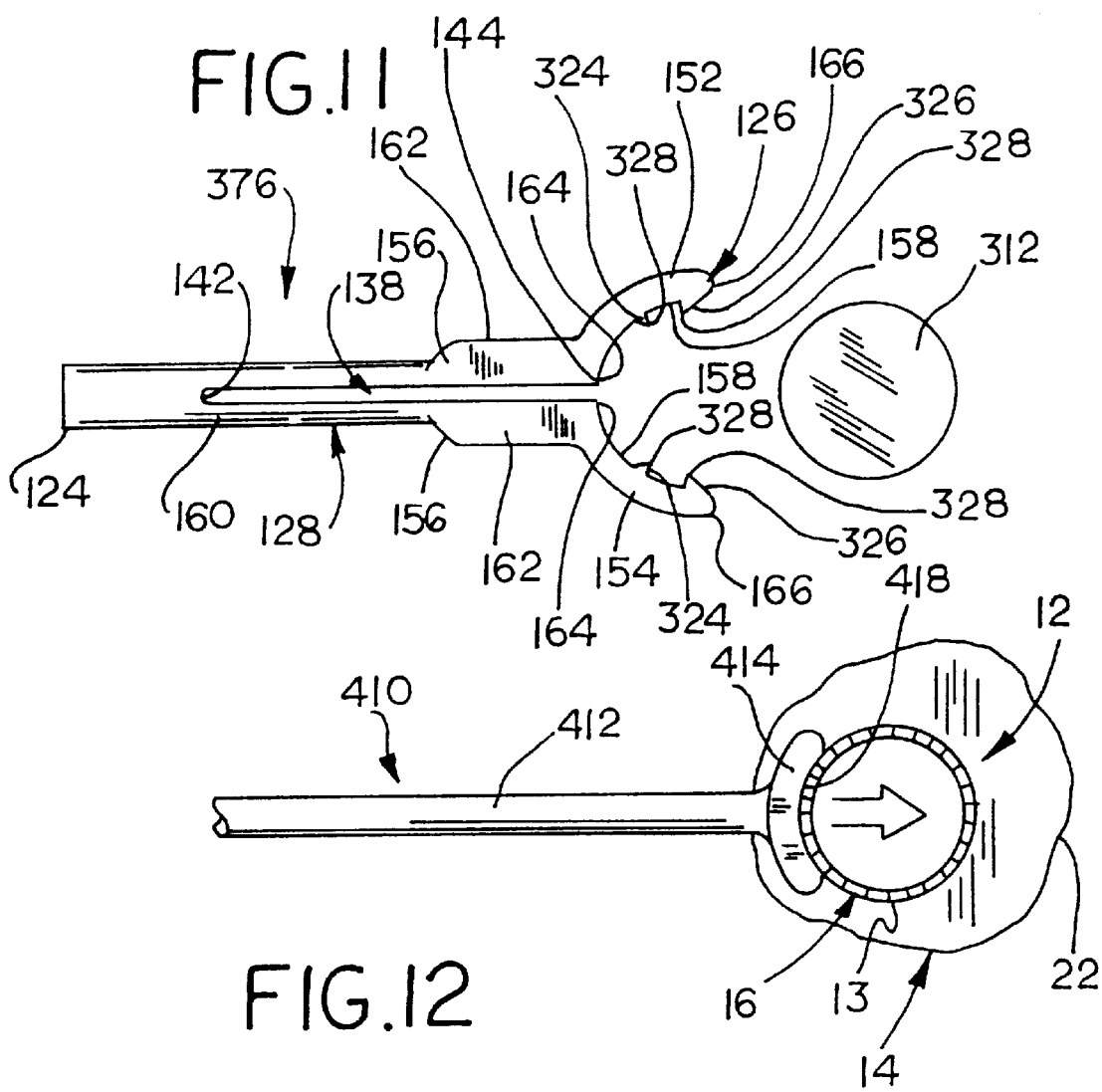

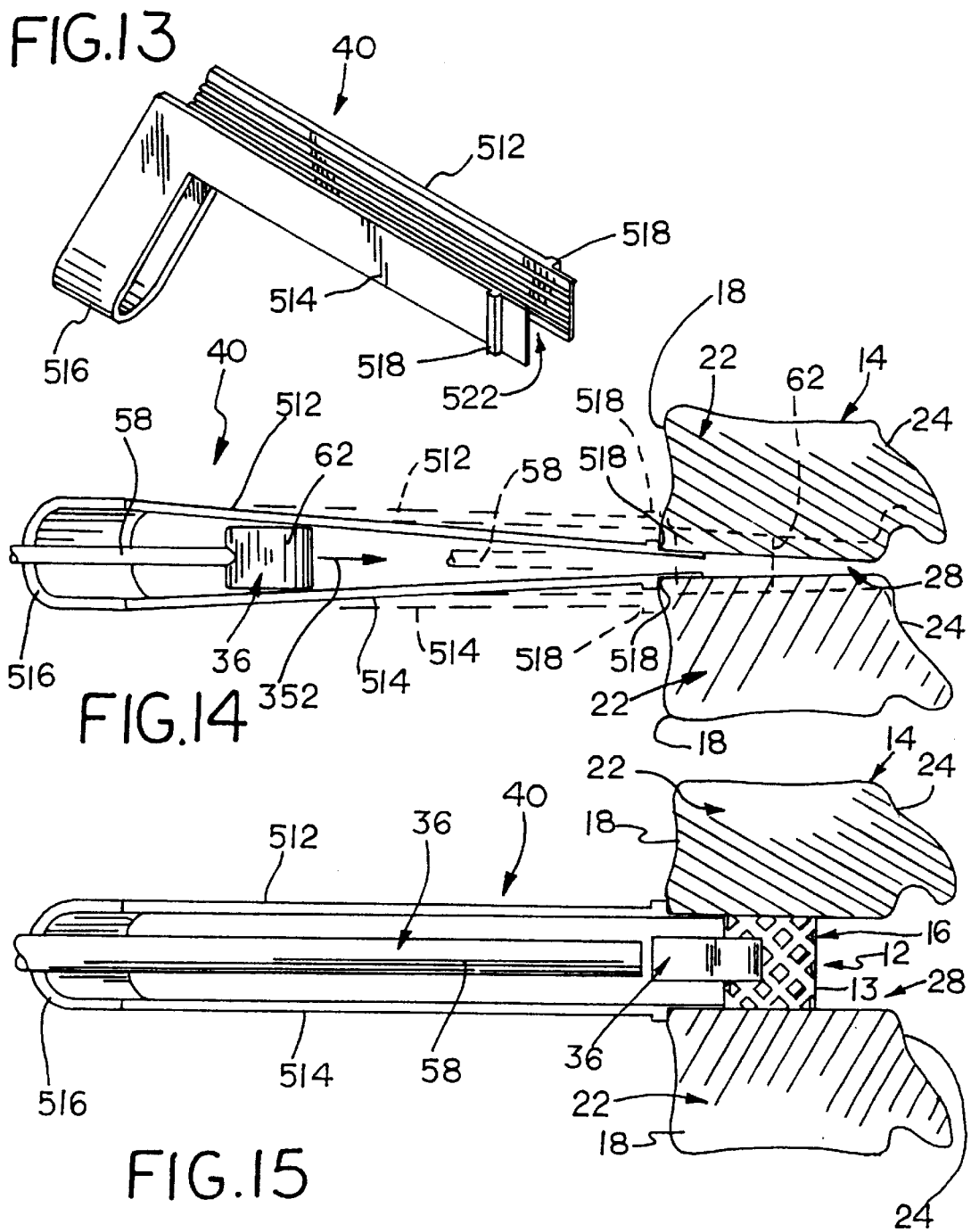

INSERTION INSTRUMENTS AND METHOD FOR DELIVERING A VERTEBRAL BODY SPACER

BACKGROUND AND SUMMARY OF THE INVENTION

This claims priority under 35 U.S.C. §119(e) of Ser. No. 60/068,205 filed Dec. 19, 1997 and Ser. No. 60/071,527 filed Jan. 15, 1998.

The present invention relates to a spacer insertion instrument, more particularly to an instrument for inserting a spacer into an anterior portion of the spine. A method is also provided for delivering a vertebrae body spacer to the spine.

Instruments for inserting spacers into a spine are known. See, for example U.S. Pat. No. 5,431,658 to Moskovich, which is incorporated herein by reference.

According to the present invention a spacer-insertion instrument is provided for delivering a spacer to a spine. The spacer-insertion apparatus comprises a handle portion, a guide coupled to the handle portion, a shaft coupled to the handle portion and extending along the guide, and a tip coupled to the shaft. The tip includes an attachment end portion that is coupled to the shaft and opposing fingers for grasping the spacer. The fingers move relative to one another to grasp the spacer when the shaft is moved to actuate the fingers.

In preferred embodiments, the tip includes a central portion that extends between the attachment end portion and the fingers and includes a slot. The slot includes a closed end and an opposite open end adjacent to the fingers. In addition, each finger includes a fixed end coupled to the central portion and an opposite free end. The fixed ends cooperate with one another to define the open end of the slot.

Each finger also includes an interior surface and an exterior surface. The interior surfaces cooperate with one another to define a space sized to receive the spacer. The interior surfaces are generally concave in shape. In addition, each finger may be formed to include at least one tooth extending into the space in accordance with embodiments of the invention.

The handle portion of the spacer-insertion apparatus includes a grip and a trigger coupled to grip and to the shaft. The trigger is movable relative to the grip. Movement of the trigger toward the grip causes movement of the fingers, pressing the fixed end portions together. Thus, the fingers to move toward one another to couple the spacer therebetween. Additionally, the handle portion includes a lock coupled to the grip. The lock includes teeth that cooperate with the trigger to limit movement of the trigger away from the grip, but permit movement of the trigger toward the grip.

According to the present invention a vertebral body insertion kit is provided. The kit includes a spanner that has a handle portion with opposite ends and a notched portion formed at one of the ends. The notched portion has a pre-determined dimension and is sized for extension into a disc space formed in a spine. The kit also includes a spacer that has a dimension approximately equal to the dimension of the notched portion and a spacer-insertion apparatus. The spacer-insertion apparatus comprises a handle portion, a guide coupled to the handle portion, a shaft coupled to the handle portion and extending along the guide, and a tip coupled to the shaft. The tip includes an attachment end portion that is coupled to the shaft and opposing fingers movable relative to one another. The fingers are adapted to grasp the spacer when the shaft is moved relative to the guide.

In preferred embodiments, the kit includes a trial that has a rod and a disc portion coupled to the rod. The disc portion has a height approximately equal to the dimension of the spacer. In addition, the kit preferably includes a facilitator formed with two guides that cooperate to define a passageway therebetween. The spacer is formed for movement between the guides in the passageway. The facilitator also includes top and bottom plates coupled to the respective guides and a jack mechanism positioned to lie between the top and bottom plates.

A method for delivering a vertebral body spacer to a disc space formed in a spine between adjacent vertebral bodies is also provided in accordance with the present invention. The method includes the steps of selecting a spacer and providing a spacer-insertion apparatus having a handle portion, a shaft coupled to the handle portion, and a tip coupled to shaft, the tip including an attachment end portion coupled to the shaft and opposing fingers movable relative to one another. The method also includes placing the fingers of the spacer-insertion apparatus about the spacer and moving the fingers toward the spacer to couple the tip and the spacer together. Additionally, the method includes inserting the tip and the spacer into the disc space, moving the fingers away from the spacer to release the spacer within the disc space, and withdrawing the fingers from the disc space.

Additional features of the invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 6 is an enlarged fragmentary view of the shaft and the tip of the spacer-insertion apparatus of FIG. 5 and the inter-vertebral spacer and showing the tip including an attachment end portion formed to couple shaft and the fingers cooperating to define a generally U-shaped space sized to receive the spacer;

FIG. 7 is an assembled top view with portions broken away of the guide, the shaft, the tip, and the spacer of FIG. 6 showing the shaft coupled to a threaded inner surface of the tip and showing the spacer positioned to lie within the U-shaped space;

FIG. 8 is a view similar to FIG. 7 following movement of the tip toward the guide pressing the fingers toward each other to couple the spacer-insertion apparatus and spacer together;

FIG. 9 is a perspective view of a tip in accordance with the present invention and a spacer including a side wall formed to include apertures and showing the tip including fingers each with an interior surface that cooperate to define a space sized to receive the spacer and a tooth extending from the interior surface into the disc space;

FIG. 10 is a top view with portions broken away of the tip and spacer of FIG. 9 showing the spacer in an attached position wherein the teeth of the fingers extend through the apertures and engage the side wall of the spacer to couple the spacer-insertion apparatus and spacer together;

FIG. 11 is a plan view of a tip in accordance with the present invention and an irregularly-shaped spacer and showing the tip including fingers each having an interior surface that cooperate to define a generally space sized to receive the spacer and spaced-apart teeth extending from the interior surface into the disc space to bite into the spacer;

FIG. 12 is a plan view of an adjuster configured to engage a spacer and guide placement of the spacer on a vertebral body;

FIG. 13 is a perspective view of a facilitator that is configured to allow for insertion of spacers and showing the facilitator including a pair of guides cooperating to define a passageway;

FIG. 14 is a side view of the facilitator of FIG. 13 in an expanded position with portions of the bone broken away, showing the trial of FIG. 4 positioned to lie in the passageway between the guides and, in phantom, the facilitator and the trial positioned to lie within the disc space;

FIG. 15 is a view similar to FIG. 14 showing the spacer-insertion apparatus of FIG. 5 extending through the passageway defined by the guides of the facilitator to position the spacer in the disc space.

DETAILED DESCRIPTION OF THE DRAWINGS

Figure 1:
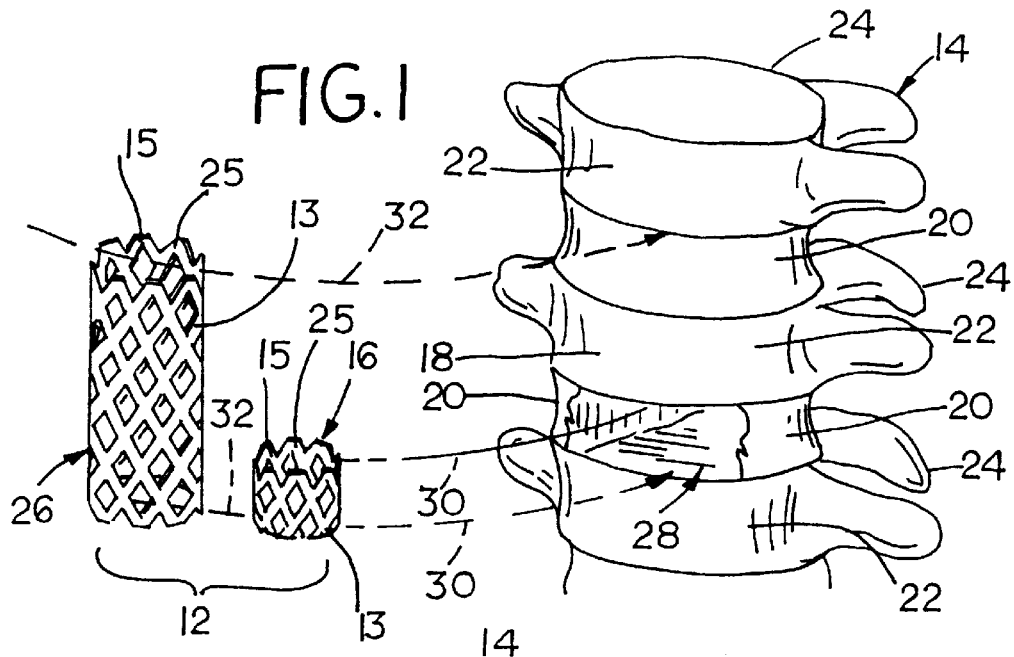
FIG. 1 is a perspective view of an anterior portion of a spine, an inter-vertebral spacer, and a vertebral body spacer and showing a portion of one disc removed from the spine to form a disc space and the inter-vertebral spacer sized for extension into the disc space.

Insertion instruments 10 are provided in accordance with the present invention for delivering vertebral body spacers 12 to a spine 14 during disc-replacement or vertebral body replacement surgery. Instruments 10 permit a surgeon to place spacers 12 into an anterior portion 18 of spine 14. This placement may be done to replace an inter-vertebral disc 20, as shown by arrows 30, or to replace a vertebral body 22, as shown by arrows 32, or multiple versions of each. Instruments 10 include a spanner 34, a trial 36, a spacer-insertion apparatus 38, and a facilitator 40.

As shown in FIG. 1, spacers 12 include inter-vertebral spacer 16 and vertebral-body spacer 26. Spacers 16, 26 are constructed of titanium mesh. Spacers 16, 26 include an outer surface 13 and an inner surface 15 that define a cavity 25 sized to house bone (not shown) such that spacers 16, 26 fuse to spine 14 to where there will be generally no movement between the two to reduce a patient's pain. In addition, apertures 17 extend between outer and inner surfaces 13, 15. Instruments 10 are also suitable for use with other forms of spacers that are also used in anterior portion 18 of spine 14. Specifically, instruments 10 are suitable for use with spacers constructed in a variety of sizes and from a variety of metals, composites, tissue, or bone, or any other type of spacer designed to be placed into spine 14 as a spinal spacer.

Figure 2:
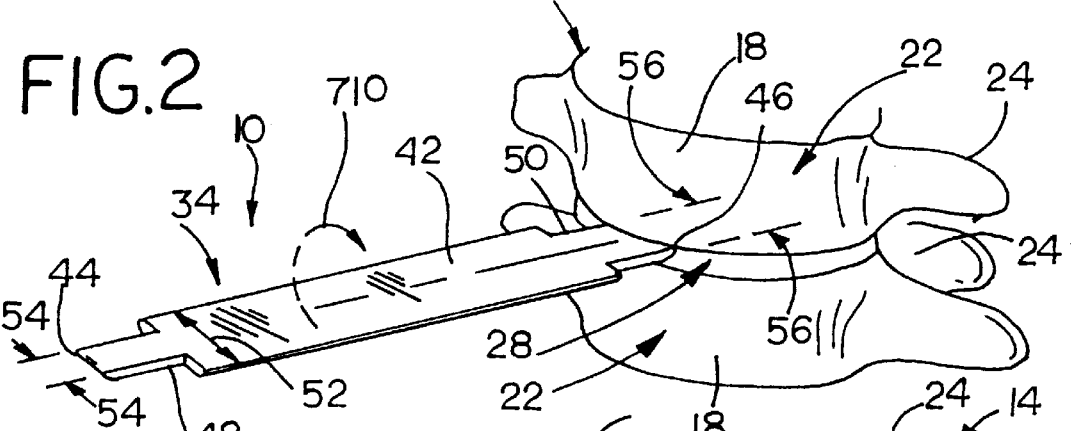
FIG. 2 is a perspective view of a spanner extending into the disc space of FIG. 1.
Figure 3:
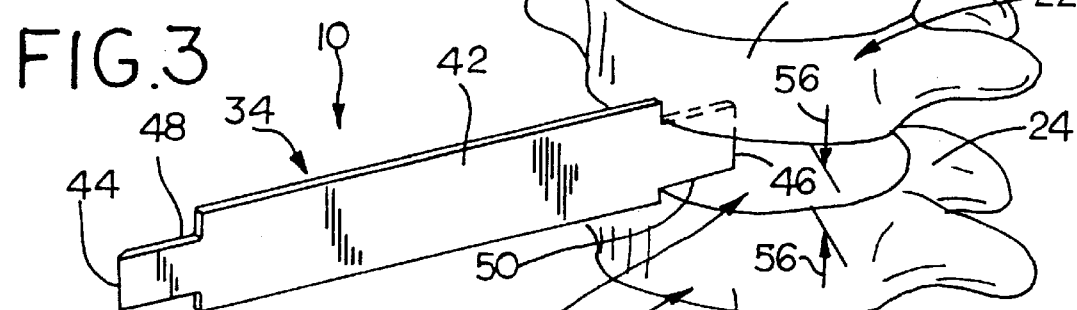
FIG. 3 is a perspective view of the spanner of FIG. 2 in a raised position and showing the spanner including a notched portion that engages an anterior cortex of the vertebral body.

Referring now to FIGS. 1–3, spine 14 includes anterior portion 18 and a posterior portion 24. In addition, spine 14 is constructed of seven cervical vertebral bodies 22, twelve thoracic vertebral bodies 22, and five lumber vertebral bodies 22. Instruments 10 of the present invention are configured to deliver spacers 12 to anterior portion 18 or posterior portion 24 of spine 14 whether it is cervical, thoracic or lumber. As shown in FIG. 1, spacers 12 that are delivered with instruments 10 in anterior portion 18 of spine 14 can be designed to replace either disc 20 or vertebral body 22.

Figure 4:
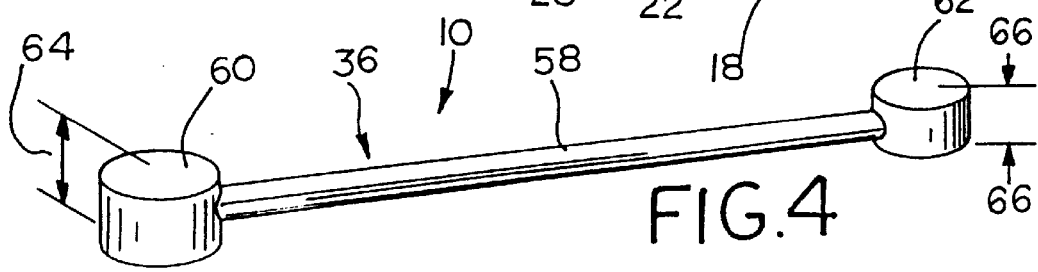
FIG. 4 is a perspective view of a trial, showing the trial including a rod and opposite disc portions formed thereon that are formed to be approximately the same size of the spacers.

Referring now to FIG. 2, spanner 34 aids the surgeon in determining the approximate size of spacer 12 that should be placed within disc space 28. In addition, spanner 34 may be placed within disc space 28 to jack open disc space 28, as shown in FIG. 4, so that surgeon can clean out remaining disc 20 within disc space 28 between vertebral bodies 22. Spanner 34 includes a handle portion 42 having opposite ends 44, 46 and notched portions 48, 50 extending from ends 44, 46 respectively. As best shown in FIG. 3, handle portion 42 of spanner 34 has a first dimension 52. Referring now to FIG. 2, notched portion 48 has a second dimension 54 that is less than first dimension 52.

Moreover, notched portion 50 has a third dimension 56 that is greater than second dimension 54 and less than first dimension 52.

As shown in FIG. 4, trial 36 mimics spacer 12 and aids the surgeon in assessing how a corresponding spacer 12 would fit into disc space 28. Trial 36 includes a rod 58 and disc portions 60, 62 on either end of rod 58. Disc portion 60 has a first height 64 and second disc portion 62 has a second height 66. Illustratively, second height 66 is less than first height 64. It is appreciated that disc portions 60, 62 may vary in height so as to mimic the size of various spacers. Disc portions 60, 62 also have a pre-determined diameter that may vary in size in accordance with the present invention. Thus, trial 36 enables a surgeon to check both the height and the diameter of disc space 28 to determine what height and diameter spacer 12 will fit in disc space 28 to engage the maximum amount of vertebral body 22. In addition, it is appreciated that trial 36 may be formed with only one disc 60 formed thereon to enable a surgeon to strike rod 58 and tap disc 60 into disc space 28.

Spacer-insertion apparatus 38 grips and delivers spacer 12 to spine 14. While only inter-vertebral spacer 16 will be discussed hereafter, it is understood that the description also applies to vertebral-body spacer 26. Instrument 38 includes a handle portion 68, a guide 70 extending from handle portion 68, a shaft 74 extending along the guide 70, and a tip 76 coupled to shaft 74 and formed to grasp spacer 16.

Figure 5:
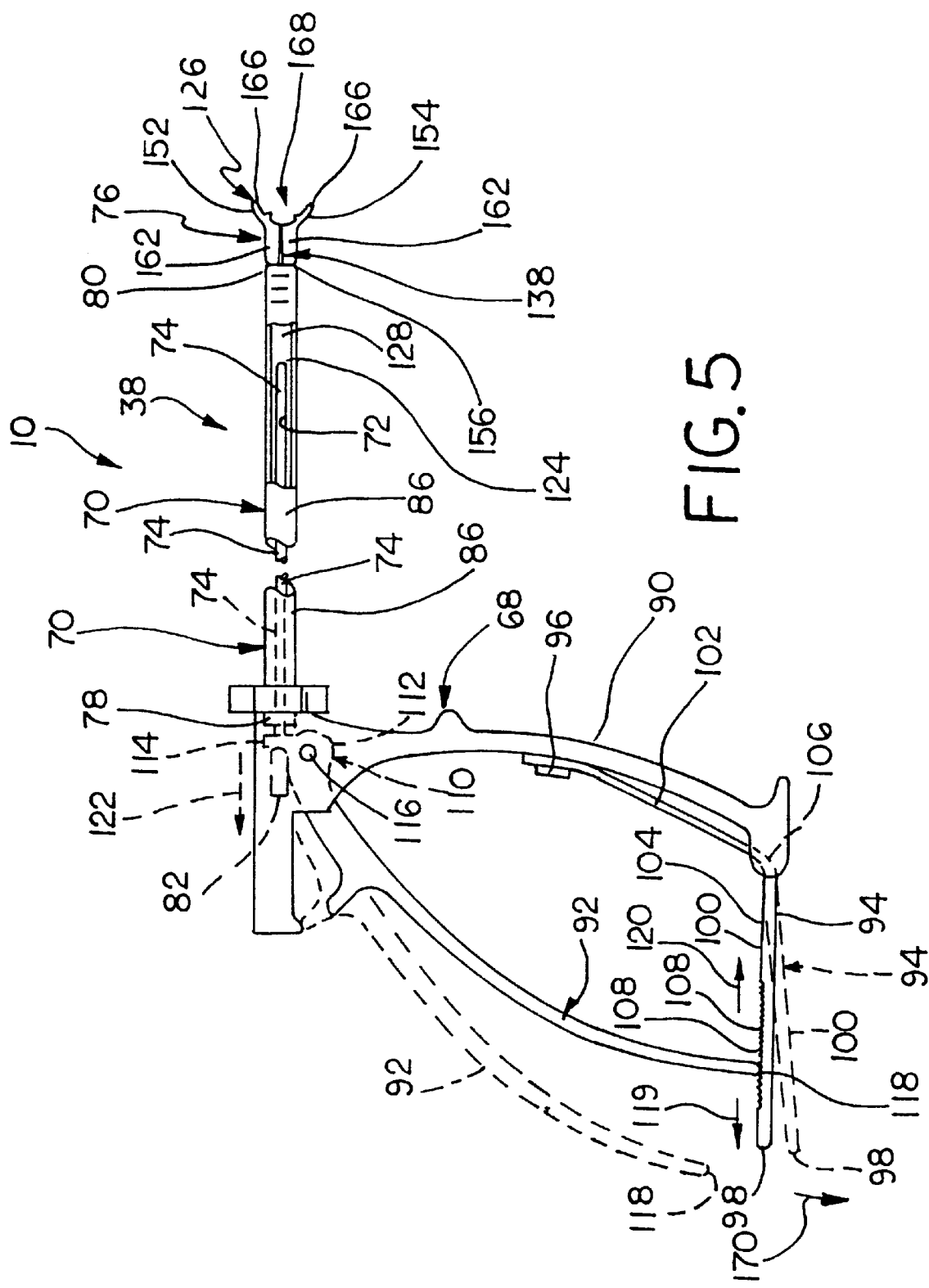
FIG. 5 is a side view of a spacer-insertion apparatus in accordance with the present invention with portions broken away showing the apparatus including a handle portion, a guide coupled to the handle portion and defining a passageway, a shaft extending through the passageway and a tip coupled to the shaft and including fingers formed to grasp the spacers of FIG. 1.

Referring now to FIG. 5, handle portion 68 includes a grip 90, a movable trigger 92, and a lock 94 coupled to grip 90. Grip 90 is stationary and formed to be grasped by a surgeon. Movable trigger 92 pivots relative to grip 90 and includes an upper end portion 110 and a lower end portion 118. Upper end portion 110 includes a grip portion 112 coupled to grip 90 by a pin 116 and a shaft portion 114 spaced apart from grip portion 112 and coupled to first end portion 78 of shaft 74. Lock 94 is coupled to grip 90 and formed to block movement of trigger 92 away from grip 90 during insertion of spacer 16 into spine 12. As shown in FIG. 5, lock 94 includes a first end portion 96 coupled to grip 90 an opposite second end portion 98, and an angled middle portion 100 extending between end portions 96, 98. Middle portion 100 of lock 94 has a generally vertical segment 102 and a generally horizontal segment 104 that meet at a joint 106. Teeth 108 extend from horizontal segment 104 adjacent to second end portion 98. Teeth are formed to cooperate with lower end portion 118 to permit movement of trigger 92 toward grip 90, as shown by arrow 120, and block movement of trigger 92 away from grip 90, as shown by arrow 119.

As shown in FIGS. 5–8, guide 70 of spacer-insertion apparatus 38 extends between handle portion 68 and tip 76. Guide 70 includes an inner end portion 78 coupled to handle portion 68 and an outer end portion 80 spaced-apart from inner end portion 78. A passageway 72 extends between inner and outer end portions 78, 80. Shaft 74 of spacer-insertion apparatus 38 extends through passageway 72 of guide 70 and includes a first end portion 82 coupled to handle portion 68, an opposite second end portion 84 spaced-apart from outer end portion 80 of guide 70, and a middle portion 86 extending between first and second end portions 82, 84. As shown in FIG. 6, second end portion 84 of shaft 74 includes threads 88 thereon.

It is understood that the length of guide 70 and shaft 74 will vary depending whether the surgeon selects an anterior or posterior approach for the surgery. Thus, spacer-insertion apparatus 38 of the present invention may be used with anterior or posterior approaches to the cervical, thoracic, or lumbar spine 14. Spacer-insertion apparatus 38 having a relatively short guide 70 and shaft 74 are used for the anterior cervical procedure. In the case of the anterior thoracic and anterior lumbar procedures, guide 70 and shaft 74 is longer than that used in the anterior cervical procedure and guide 70 has an increased diameter to provide strength. Finally, in the posterior thoracic or lumbar procedure, guide 70 and shaft 74 are sized in between guides 16 and shafts 20 used in the anterior cervical procedure and the anterior thoracic and anterior lumbar procedures.

As shown in FIGS. 5–8, tip 76 of spacer-insertion apparatus 38 is coupled to shaft 74 and permits the surgeon to effectively grip spacer 16. Referring now to FIG. 6, tip 76 includes an attachment end portion 124 formed to couple shaft 74, an opposite clamp end portion 126, and a central portion 128 that extends between attachment and clamp end portions 124, 126. Attachment end portion 124 is formed to define an opening into a cavity 136. Threads 134 extend about an inner surface 132 in cavity 136 to couple threads 88 of shaft 74. It is appreciated that attachment end portion 124 may be coupled to shaft 74 in a variety of manners and tip and shaft, may in fact, be formed as a unitary member.

Central portion 128 of tip 76 extends between attachment and clamp end portions 124, 126 and has an outer surface 130 sized for movement within passageway 72 of guide 70. In addition, as shown in FIGS. 6–8, central portion 128 includes a slot 138 extending through outer surface 130. Slot 138 has a closed end 142, an opposite open end 144 adjacent to clamp end 126, and a middle portion 146 extending between ends 142, 144. Middle portion 146 includes opposite sides 148, 150 that cooperate to define a pre-determined normal width 142 of slot 138. It is appreciated that normal width 140 of slot 138 may vary.

As shown in FIG. 6, clamp end portion 126 of tip 76 includes fingers 152, 154 extending from respective sides 148, 150 of slot 138. Each finger 152, 154 includes a fixed end portion 164 coupled to an outer end portion 162 of central portion 128 and an opposite free end 166. As best shown in FIG. 7, fixed end portions 164 cooperate to define open end 144 of slot 138. In addition, each finger 152, 154 includes an interior surface 158 and an exterior surface 159. Interior surfaces 158 cooperate to define a generally U-shaped space 168 sized to receive spacer 16 therein. Fingers 152, 154 are movable relative to one another and adapted to grasp spacer 16 when shaft 74 is moved toward handle portion 68 to actuate fingers 152, 154. It is appreciated that fingers 152, 154 may be moved together when shaft 74 is pushed, rotated, or otherwise moved relative to the guide 70 in accordance with the present disclosure. Interior surface 158 of fingers 152, 154 are configured to provide generally uniform contact between tip 76 and spacer 16. Spreading the force of contact of tip 76 over outer surface 13 of spacer 16 decreases the risk of spacer 16 deformation during implantation between vertebrae 22. It is appreciated that the dimensions of interior surfaces 158 of fingers 152, 154 may vary to accommodate spacers 12 of various sizes.

To assemble spacer-insertion apparatus 38 of the present invention, threaded second end portion 84 of shaft 74 is inserted into threaded cavity 136 of attachment end 124. Tip 76 is rotated until threads 88 of shaft 74 are coupled to threads 134. Shaft 74 is configured for use with a variety of tips 22 having fingers 152, 154 of various sizes. Thus, a kit is contemplated wherein spacer-insertion apparatus 38 includes various tips that are interchangeable with shaft 74.

For example, referring now to FIGS. 9 and 10, tip 276 is provided in accordance with the present invention. Tip 276 is formed similarly to tip 76 and like reference numerals will be used to denote like components. Tip 276 is configured for use with handle portion 68 and guide 70 to form a spacer-insertion instrument 238 in accordance with the present invention. Referring to FIG. 9, tip 276 includes opposing fingers 152, 154 as previously discussed. Each finger 152, 154 includes a tooth 278 extending outwardly from interior surface 158. Teeth 278 are generally triangular in shape and sized for extension through aperture 17 and engagement with edges 19 defining aperture 17 of spacer 16. As shown in FIG. 10, teeth 278 extend through apertures 17 and engage edges 19 to prevent spacer 16 from sliding out from space 168 between fingers 152, 154. It is appreciated that tip 278 may be used to couple a variety of spacers having apertures 17 that are defined in a variety of shapes. Further, it is appreciated that interior surface 158 of fingers 152, 154 may be formed to include greater than one tooth 278 formed in a variety of shapes and sizes to cooperate with edges 19 of spacer 16.

Tip 376 is also provided in accordance with the present invention and is shown in FIG. 11. Tip 376 is formed similarly to tip 76, and like reference numerals will be used to denote like components. Tip 376 is configured for use with irregularly shaped objects, such as bone 312. Tip 376 includes a first tooth 324 extending into space 168 from interior surface 158 of each finger 152, 154. First tooth 324 is spaced apart between fixed and free end portions 164, 166. In addition, tip 376 includes a second tooth 326 extending into space 168 from interior surface 158 of each finger 152, 154 adjacent to free end portion 166. Teeth 324, 326 each include a pointed end portion 328 to dig into bone 312. Teeth 324, 326 lock into and hold bone 312 to prevent bone 312 from sliding out of space 168 between fingers 152, 154. It is appreciated that teeth 324, 326 may be formed in a variety of shapes and sizes and be positioned to lie in a variety of locations on interior surface 158 of fingers 152, 154.

As best shown in FIG. 12, an adjuster 410 is also provided in accordance with the present invention. Adjuster 410 is used to hold spacer 12 in a stationary portion during withdrawal of spacer-insertion apparatus 38 from disc space 28. In addition, adjuster 410 may be used to further position spacer 12 upon vertebral body 22. Adjuster 410 includes a handle portion 412 and a platform 414 extending from handle portion 412. Platform 414 includes a generally concave contact surface 418 that is formed to cooperate with outer surface 13 of spacer 12. It is appreciated, however, that platform 414 may be formed in a variety of manners to cooperate with spacers formed in various shapes.

As shown in FIGS. 13–15, facilitator 40 is provided to aid the surgeon in inserting trial 62 into disc space 28. Facilitator 40 includes two guides 512, 514 joined by an elbow piece 516 as described in U.S. Pat. No. 5,431,658 to Moskovich, which is incorporated herein by reference. Guides 512, 514 each include a lip 518 and cooperate to define a passageway 522 therebetween.

Figure 16:
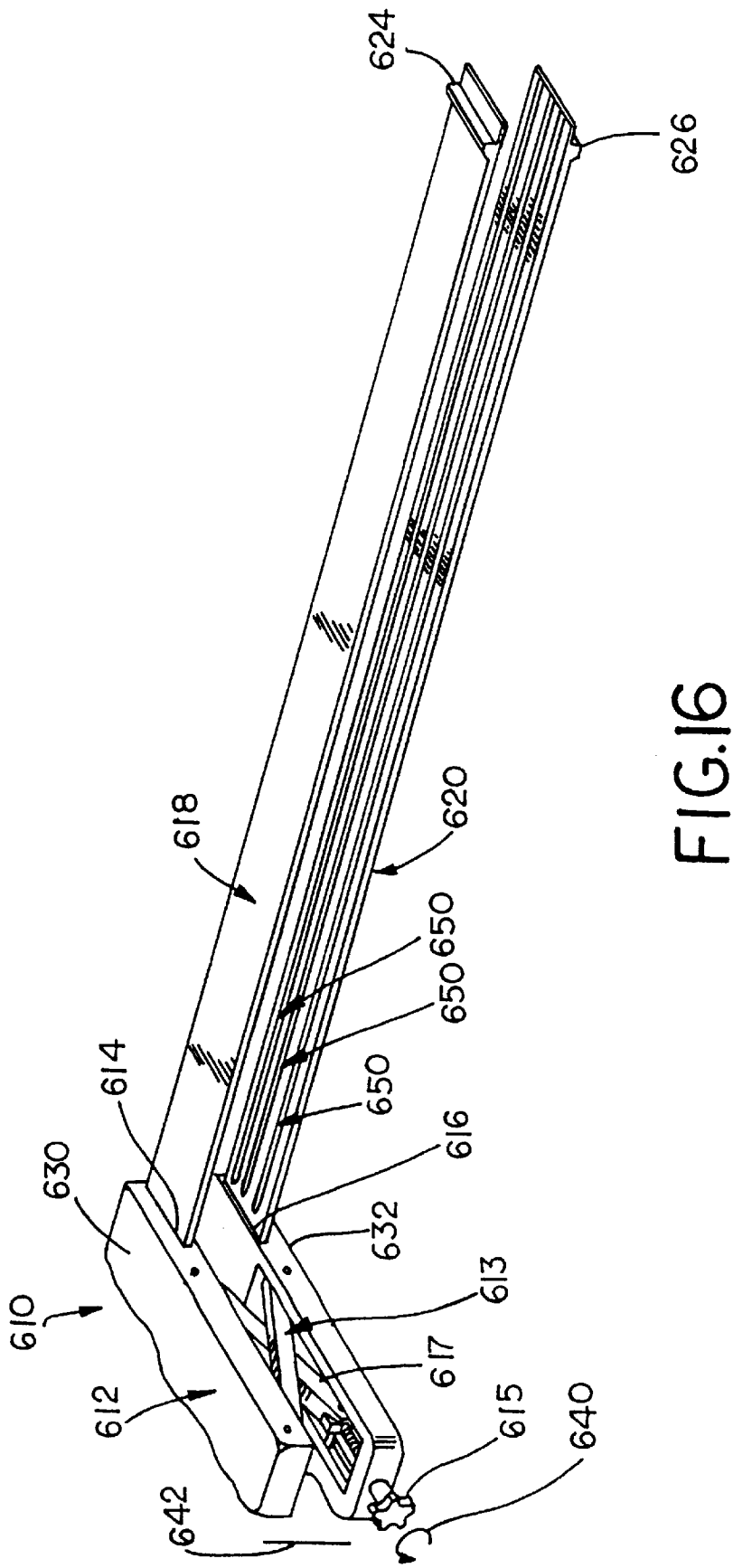
FIG. 16 is a perspective view of a facilitator in accordance with the present invention that is used for anterior procedures, showing the facilitator including top and bottom plates, a jack mechanism coupled to the top and bottom plates, and spaced apart guides coupled to the top and bottom plates.

In addition, a facilitator 610 is provided and illustrated in FIG. 16 to aid the surgeon in inserting trial 62 into disc space 28. Facilitator 610 is modular and includes a handle 612, a jack mechanism 613 coupled to handle 612, and guides 618, 620 that extend from handle 612. Handle 612 includes a top plate 630 and a bottom plate 632. Top and bottom plates 630, 632 include slots 614, 616 therein respectively. Jack mechanism 613 incudes a movable X-shaped support 617 and a knob 615 coupled to support 615. Knob 615 is rotated as shown by arrow 640 to cause top and bottom plates 630, 632 to move away from one another, as shown by arrow 642. Thus, guides 618, 620 can be moved so as to create a passageway 654 therebetween that is sized to receive a spacers of various sizes.

Guides 618, 620 are separate from handle 612 and thus are removable from slots 614, 616 of top plates 630, 632. Guides 618, 620 constrain the interbody spacer or prosthesis 12 as it is inserted by the spacer-insertion apparatus 38 into disc space 28. Guides 618, 620 also simultaneously distract the intervertebral space 28 to permit entry and placement of spacer or prosthesis 12 under the desired (pre-determined) tension. Guides 618, 620 are described in U.S. Pat. No. 5,431,658 to Moskovich, which is incorporated herein by reference. As shown in FIG. 16, guides 618, 620 each are formed to include an outer surface 680 and an inner surface 682. A lip 622 is formed on outer surface 680 of each guide 618, 620. In addition, inner surface 682 is formed to include generally parallel grooves 650. Facilitator 610 provides the surgeon with the ability to form a small incision since guides 618, 620 may be pushed together to form a low profile to match the small incision. In addition, facilitator 610 can be used as a skid to deliver a large spacer for a vertebral body replacement (not shown).

When replacing disc 20, the surgeon first removes damaged disc 20 to create a disc space 28 between adjacent vertebral bodies 22. Once disc space 28 is formed, one notched portion 48, 50 of spanner 24 is selected, as shown in FIGS. 2 and 3. Notched portion 48, 50 is selected that best fit the size of disc space 28 to aid the surgeon in determining the approximate size of spacer 16 to select. As best shown in FIG. 2, notched portion 50 is inserted into disc space 28 such that handle portion 42 is aligned with spine 14. Handle portion 42 is then rotated as shown by arrow 710 until handle portion 42 assumes a generally vertical position, as shown in FIG. 3. Once in the generally vertical position, spanner 34 has jacked open disc space 28 to third dimension 56.

At this time, the surgeon is able to test disc space 28 to gauge approximately what size spacer 12 may be placed within space 28 as well as to clean any remaining disc material from disc space 28. The dimensions of disc space 28 vary widely from patient to patient. Therefore, trial 36 is provided to mimic spacer 12. As best shown in FIG. 14, trial 36 is used in conjunction with facilitator 40 to gauge the size of disc space 28 so that the surgeon can select the properly sized spacer 12.

Illustratively, facilitator 40 is inserted into disc space 28 so that lips 518 engage vertebral bodies 22. Disc portion 60 of trial 36 is then inserted into passageway 416 of facilitator 40. Disc portion 60 moves, as shown by arrow 352 between guides 512, 514 toward lips 518 of facilitator 40. As disc portion 60 moves through passageway 522, lips 518 move apart, as shown in phantom in FIG. 14, to jack disc space 28 open. As shown in phantom in FIG. 14, disc portion 60 extends into disc space 28. It is understood that any number of disc portions having a variety of sizes may pass through passageway 522 into disc space 28 until the surgeon is satisfied that the disc portion best matches the size of disc space 28. Thus, trial 36 enables a surgeon to check both the height and the diameter of disc space 28 to determine what height and diameter spacer 16 will fit in disc space 28 to engage the maximum amount of vertebral body 22.

Once a particularly sized disc portion 60 is selected, the surgeon then selects a spacer 12 that is substantially equivalent in size to disc portion 60. A tip 76, 176, 276 is then selected that best corresponds to selected spacer 12. While tip 76 will be discussed hereafter, it is understood that the description applies to tip 176 and 276 as well. As best shown in FIG. 6, threaded end portion 84 of shaft 74 is coupled to threaded inner surface 132 of tip 76 to assemble spacer-insertion apparatus 10 38 accordance with the present invention.

To use spacer-insertion apparatus 38 of the present invention, fingers 152, 154 of tip 76 are placed about outer surface 13 of spacer 16 so that each interior surface 158 faces spacer 16. Referring now to FIG. 5, the surgeon squeezes trigger 92 as shown by arrow 120. Referring now to FIG. 7, movement of trigger 92 relative to grip 90 causes shaft 74 to move as shown by arrow 122 in passageway 72 away from outer end portion 80. As shaft 74 pulls back, tip 76 moves further into passageway 72. As shown in FIG. 8, tapered edges 156 of tip 76 slide into passageway 72 of guide 70 to press fingers 152, 154 together and lock clamp end portion 126 on spacer 16. The surgeon is then free to push, pull, move laterally, and even rotate spacer 16 relative to spine 14.

To insert spacer 12 into disc space 28, spacer-insertion apparatus 38 is used in conjunction with facilitator 40 or 610. While facilitator 40 will be discussed hereafter, it is understood that spacer-insertion apparatus 38 may be used with facilitator 610, particularly in anterior lumbar procedures. As shown in FIG. 15, tip 76 and spacer 12 are inserted into passageway 522 of facilitator 40. Tip 76 moves through passageway 522 similarly to disc portion 60 of trial 36 until tip 76 is positioned to lie within disc space 28. Once spacer 16 is placed, second end portion 98 of lock 94 is pulled away from trigger 92 in direction of arrow 170. Trigger 92 is then unlocked, causing fingers 152, 154 to move away from one another to release spacer 16 within spine 14. Referring now to FIG. 12, before tip 76 is withdrawn from disc space 28, adjuster 410 is inserted into disc space 28 so that platform 414 engages spacer 16. Platform 414 is held against spacer 16 as tip 76 is pulled out of disc space 28. In addition, surgeon may wish to move spacer 16 upon vertebral body 22. In such a case, the surgeon must only tap on handle portion 412.

Cervical, posterior, and anterior insertions all follow the same basic steps. It is understood that while spacer-insertion apparatus 10 is illustrated in use with facilitator 40 and adjuster 410, spacer-insertion apparatus 38 can be used alone for in the insertion of spacer 12 into disc-space 28 or with any number of guides.

Although the invention has been described in detail with reference to a preferred embodiment, variations and modifications exist within the scope and spirit of the invention as described and defined in the following claims.

What is claimed is:

1. A spacer-insertion instrument for delivering a spacer to a spine, comprising:
   a handle portion,
   a guide coupled to the handle portion,
   a shaft coupled to the handle portion and extending along the guide, and
   a tip including an attachment end portion coupled to the shaft and opposing fingers movable relative to one another and adapted to grasp the spacer when the shaft is moved to actuate the fingers,
   wherein each finger includes an interior surface and an exterior surface and the interior surfaces cooperate to define a space sized to receive the spacer therein, and
   wherein each finger includes a tooth extending into the space.

2. A spacer-insertion instrument for delivering a spacer to a spine, comprising:
   a handle portion,
   a guide coupled to the handle portion,
   a shaft coupled to the handle portion and extending along the guide, and
   a tip including an attachment end portion coupled to the shaft and opposing fingers movable relative to one another and adapted to grasp the spacer when the shaft is moved to actuate the fingers,
   wherein each finger includes an interior surface and an exterior surface and the interior surfaces cooperate to define a space sized to receive the spacer therein, and
   wherein each finger includes two spaced-apart teeth extending into the space.

3. A spacer-insertion instrument for delivering a spacer to a spine, comprising:
   a handle portion,
   a guide coupled to the handle portion,
   a shaft coupled to the handle portion and extending along the guide, and
   a tip including an attachment end portion coupled to the shaft and opposing fingers movable relative to one another and adapted to grasp the spacer when the shaft is moved to actuate the fingers,
   wherein the handle portion includes a grip and a trigger coupled to the grip and to the shaft and movement of the trigger toward the grip causes the fingers to move toward one another.

4. The apparatus of claim 3, wherein the tip includes a central portion extending between the attachment end portion and the fingers.

5. The apparatus of claim 4, wherein the central portion is formed to include a slot.

6. The apparatus of claim 5, wherein the slot includes a closed end and an open end adjacent to the fingers.

7. The apparatus of claim 6, wherein each finger includes a fixed end coupled to the central portion and an opposite free end and the fixed ends cooperate to define the open end of the slot.

8. The apparatus of claim 4, wherein each finger includes an interior surface and an exterior surface and the interior surfaces cooperate to define a space sized to receive the space therein.

9. The apparatus of claim 8, wherein the interior surfaces are generally concave in shape.

10. The apparatus of claim 3, wherein the handle portion includes a lock coupled to the grip and the lock is formed to limit movement of the trigger away from the grip.

11. The apparatus of claim 10, wherein the lock includes teeth that cooperate with the trigger to permit movement of the trigger toward the grip.

12. The apparatus of claim 3, wherein the guide includes an inner portion coupled to the handle portion and an outer end portion and the tip is coupled to the shaft and extends away from the outer end portion.

13. A vertebral body insertion kit, the kit comprising:
   a spanner including a handle portion having opposite ends and a notched portion formed at one of the ends, the notched portion having a pre-determined dimension and sized for extension into a space formed in a spine,
   a spacer having a dimension approximately equal to the dimension of the notched portion, and
   a spacer-insertion apparatus comprising a handle portion, a guide coupled to the handle portion, a shaft coupled to the handle portion and extending along the guide, and a tip including an attachment end portion coupled to the shaft and opposing fingers movable relative to one another and adapted to grasp the spacer when the shaft is moved relative to the guide.

14. The kit of claim 13, further comprising a trial including a rod and a disc portion coupled to the rod, the disc portion having a height approximately equal to the dimension of the spacer.

15. The kit of claim 13, further comprising a facilitator formed to include two guides that cooperate to define a passageway therebetween and the spacer is formed for movement between the guides.

16. The kit of claim 15, wherein the facilitator includes top and bottom plates coupled to the respective guides and a jack mechanism positioned to lie between the top and bottom plates.

17. The apparatus of claim 13, wherein each finger includes an interior surface and an exterior surface and the interior surfaces cooperate to define a space sized to receive the spacer therein.

18. The apparatus of claim 17, wherein each finger includes at least one tooth extending into the space.

19. A method for delivering a vertebral body spacer to a disc space formed in a spine between adjacent vertebral bodies, the method comprising the steps of:
   selecting a spacer,
   providing a spacer-insertion apparatus having (i) a handle portion which includes a grip and a trigger, (ii) a shaft coupled to the trigger of the handle portion, and (iii) a tip coupled to the shaft, the tip including an attachment end portion coupled to the shaft and opposing fingers movable relative to one another,
   placing the fingers about the spacer,
   moving the trigger toward the grip so as to cause the fingers to move toward the spacer to couple the tip and the spacer together,
   inserting the tip and the spacer into the disc space,
   moving the trigger away from the grip so as to cause the fingers to move away from the spacer to release the spacer within the disc space, and
   withdrawing the fingers from the disc space.

* * * * *